(12) United States Patent
Weffers-Albu et al.

(10) Patent No.: US 10,772,528 B2
(45) Date of Patent: Sep. 15, 2020

(54) REHABILITATION SYSTEM AND METHOD (71) Applicant: KONINKLIJKE PHILIPS N.V., Eindhoven (NL)

(72) Inventors: Mirela Alina Weffers-Albu, Boukoul (NL); Raymond Van Ee, Geldrop (NL)

(73) Assignee: Koninklijke Philips N.V., Eindhoven (NL)

(*) Notice: Subject to any disclaimer, the term of this patent is extended or adjusted under 35 U.S.C. 154(b) by 678 days.

(21) Appl. No.: 15/310,301

(22) PCT Filed: May 27, 2015

(86) PCT No.: PCT/EP2015/061752
§ 371 (c)(1),
(2) Date: Nov. 10, 2016

(87) PCT Pub. No.: WO2015/185420
PCT Pub. Date: Dec. 10, 2015

(65) Prior Publication Data
US 2017/0143229 A1 May 25, 2017

(30) Foreign Application Priority Data
Jun. 3, 2014 (EP) .................................. 14170891

(51) Int. Cl.
*A61B 5/0482* (2006.01)
*A61B 5/00* (2006.01)
(Continued)

(52) U.S. Cl.
CPC .......... *A61B 5/0482* (2013.01); *A61B 5/0488* (2013.01); *A61B 5/4041* (2013.01);
(Continued)

(58) Field of Classification Search
CPC ..... A61B 5/0476; A61B 5/0478; A61B 5/048; A61B 5/0482; A61B 5/0484; A61B 5/04842; A61B 5/04845; A61B 5/04847
See application file for complete search history.

(56) References Cited

U.S. PATENT DOCUMENTS 4,800,893 A  1/1989 Ross et al.
4,928,696 A  5/1990 Henderson et al.
(Continued)

FOREIGN PATENT DOCUMENTS

CN  102138860 B  8/2011
CN  102488515 A  6/2012
(Continued)

OTHER PUBLICATIONS

Mima et al. "Coherence between Cortical and Muscular Activities after Subcortical Stroke." Stroke. Nov. 2001;32(11):2597-601. (Year: 2001).*

(Continued)

*Primary Examiner* — Meredith Weare (57) ABSTRACT

The present invention relates to a rehabilitation system (10) for a patient (24) suffering from a damaged muscle and/or nerve, said system (10) comprising: a brain activity sensor (14) for measuring a patient's brain activity related to controlling the damaged muscle and/or nerve; —a muscle sensor (18) for measuring a muscular activity of the damaged muscle and/or a neural activity of the damaged nerve; a display (22) for displaying a representation (34) of an affected body part of the patient (24); and a control unit (20) for determining an intended movement of the affected body part in which the damaged muscle and/or nerve is arranged, and for controlling the display (22) to display a representation (36) of the intended movement, wherein the control unit (20) is configured to determine the intended movement based on the patient's brain activity measured by the brain (Continued)

activity sensor (14) and based on the muscular and/or neural activity of the damaged muscle and/or nerve measured by the muscle sensor (18).

18 Claims, 3 Drawing Sheets

(51) Int. Cl.
| | |
|---|---|
| *A61B 5/0488* | (2006.01) |
| *G06F 3/01* | (2006.01) |
| *A61N 1/36* | (2006.01) |
| *A61F 7/00* | (2006.01) |
| *A61H 23/02* | (2006.01) |
| *G09B 5/06* | (2006.01) |

(52) U.S. Cl.
CPC .......... *A61B 5/4519* (2013.01); *A61B 5/6814* (2013.01); *A61B 5/6828* (2013.01); *A61B 5/6831* (2013.01); *A61B 5/744* (2013.01); *A61F 7/00* (2013.01); *A61H 23/02* (2013.01); *A61N 1/36003* (2013.01); *G06F 3/015* (2013.01); *G09B 5/06* (2013.01); *A61B 2505/09* (2013.01); *A61H 2201/02* (2013.01)

(56) References Cited

U.S. PATENT DOCUMENTS

| | | | |
|---|---|---|---|
| 5,336,269 A | | 8/1994 | Smits |
| 5,692,517 A | * | 12/1997 | Junker ................ A61B 5/0482 600/545 |
| 6,171,239 B1 | | 1/2001 | Humphrey |
| 10,271,768 B1 | * | 4/2019 | Murali ..................... A61B 5/11 |
| 2003/0093129 A1 | | 5/2003 | Nicolelis et al. |
| 2004/0073414 A1 | | 4/2004 | Bienenstock et al. |
| 2004/0267320 A1 | | 12/2004 | Taylor et al. |
| 2006/0189901 A1 | | 8/2006 | Flaherty et al. |
| 2006/0195042 A1 | | 8/2006 | Flaherty |
| 2006/0206161 A1 | | 9/2006 | Nicoleilis et al. |
| 2007/0016265 A1 | * | 1/2007 | Davoodi .................... A61F 2/68 607/48 |
| 2008/0287820 A1 | * | 11/2008 | Ignagni ................ A61N 1/3601 600/529 |
| 2009/0221928 A1 | * | 9/2009 | Einav .................. A61B 5/0484 600/544 |
| 2010/0022351 A1 | | 1/2010 | Lanfermann et al. |
| 2011/0004126 A1 | * | 1/2011 | Einav .................. G06F 19/3481 600/595 |
| 2011/0213266 A1 | | 9/2011 | Williams et al. |
| 2011/0295338 A1 | | 12/2011 | Rickert et al. |
| 2012/0130266 A1 | * | 5/2012 | Mathan ................ A61B 5/4088 600/544 |
| 2012/0265080 A1 | * | 10/2012 | Yu ............................ A61B 5/04 600/484 |
| 2014/0114687 A1 | * | 4/2014 | Frank .................. G06F 19/3481 705/3 |
| 2014/0303508 A1 | | 10/2014 | Plotnik-Peleg et al. |

FOREIGN PATENT DOCUMENTS

| | | |
|---|---|---|
| CN | 103407588 A | 11/2013 |
| EP | 2664356 A1 | 11/2013 |
| JP | 2007020835 A | 2/2007 |
| WO | 2007141680 A1 | 12/2007 |
| WO | 2008008849 A2 | 1/2008 |

OTHER PUBLICATIONS

Elmenreich et al. "Fusion of Heterogeneous Sensors Data." 2008 International Workshop on Intelligent Solutions in Embedded Systems. Jul. 10-11, 2008. (Year: 2008).*

Lalitharatne et al. "Towards Hybrid EEG-EMG-Based Control Approaches to be Used in Bio-Robotics Applications: Current Status, Challenges and Future Directions." Paladyn, Journal of Behavioral Robotics, vol. 4, Issue 2. 2013. (Year: 2013).*

"Electroencephalography." Wikipedia. Apr. 1, 2014. https://web.archive.org/web/20140401022121/https://en.wikipedia.org/wiki/Electroencephalography (Year: 2014).*

"EEG and EMG in Rehabilitation." ANT Neuro, May 28, 2014. https://web.archive.org/web/20140528115526/https://www.ant-neuro.com/show-case/eeg-and-emg-rehabilitation (Year: 2014).* von Carlowitz-Ghori et al. "Corticomuscular Coherence in Acute and Chronic Stroke." Clin Neurophysiol. Jun. 2014;125(6):1182-91. Epub Nov. 16, 2013. (Year: 2013).*

"Find a Rehab Center", Downloaded From https://www.christopherreeve.org/living-with-paralysis/rehabilitation/find-a-rehab-center on Nov. 9, 2016, 8 Pages.

* cited by examiner

REHABILITATION SYSTEM AND METHOD

CROSS-REFERENCE TO PRIOR APPLICATIONS

This application is the U.S. National Phase application under 35 U.S.C. § 371 of International Application No. PCT/EP2015/061752, filed on May 27, 2015, which claims the benefit of European Patent Application No. 14170891.7, filed on Jun. 3, 2014. These applications are hereby incorporated by reference herein.

FIELD OF THE INVENTION

The present invention relates to a rehabilitation system for a patient suffering from a damaged muscle and/or nerve. The present invention particularly relates to a rehabilitation system that addresses patients with a healthy brain activity but an impeded muscular activity, wherein the system helps such patients to exercise the movement of their impaired limb. Further, the present invention relates to a corresponding method for rehabilitating a patient.

BACKGROUND OF THE INVENTION

A general characteristic common to patients suffering from temporary paralysis due to trauma, hernia, longtime lying in bed, or just simply old age is the fact that although such patients may have a healthy neuro-activity necessary for limbic motion, their muscles and/or nerves are damaged.

Rehabilitation for damaged muscles and/or nerves is currently done mainly in rehabilitation centers where patients are under the care of physiatrists, rehab nurses, occupational therapists and physical therapists and undergo specific physiotherapy programs aiming at recovering the damaged element in the muscle and/or nerve. Physical therapists also use hot and/or cold packs as well as ultrasound systems which use high frequency waves to produce heat.

The costs associated with muscle nerve regeneration can be enormous. For instance, "according to statistics reported by the Foundation for Spinal Cord Injury Prevention and Cure, the lifetime medical costs for paraplegia are $1 million. The lifetime medical costs for quadriplegia range from $1.5 million to $3 million. The statistics do not include lost wages or other financial losses" (http://www.georgiaaccidentlaws.com). Effective, but cost-saving rehabilitation systems for the home use are therefore desirable.

US 2011/0213266 A1 discloses a closed loop, neural activity triggered rehabilitation device and method for facilitating recovery of a patient from the effects of a sensory motor disability. The device includes a sensor system positionable adjacent the brain of the patient for detecting neural signals. A functional stimulation component is operatively connectable to at least one body part, such as a muscle or a nerve. The functional stimulation component stimulates the at least one body part in response to the neural signals detected. A sensory stimulation module is operatively connected to the patient to provide sensory feedback thereto.

While such closed loop systems have shown advantageous recovery effects for the patients, the recovery of the patient still progresses very slowly, with many set-backs and very small steps forward that are difficult, if not impossible, to perceive by the patient especially in the beginning Not being able to perceive the benefits of the treatment commonly leads to patient discouragement, lack of trust and adherence to the program or device, thereby impeding the rehabilitation process. Many patients expect a very fast recovery and if no such fast recovery may be perceived by the patient, they mistrust the functionality of the device. Known devices are often lacking to give the patients a feedback about the recovery process as well as to support the patients to exercise the movement of their impaired limb. User-adherence to such devices is therefore in most of the cases quite low.

Thus, there is still room for improvement.

US 2006/0195042 A1 discloses a system and method for a biological interface system that processes multicellular signals of a patient and controls one or more devices. The system includes a sensor that detects the multicellular signals and a processing unit for producing the control signal based on the multicellular signals. The system further includes an automated configuration routine that is used to set or modify the value of one or more system configuration parameters.

U.S. Pat. No. 5,692,517 A discloses a method and apparatus for assisting a user to control a device in response to a combination of electroencephalographic and electromyographic potentials.

SUMMARY OF THE INVENTION

It is an object of the present invention to provide a rehabilitation system for a patient suffering from damaged muscles and/or nerves, wherein the system substantially alleviates or overcomes the above mentioned problems. In particular, it is an object of the present invention to provide a rehabilitation system which is applicable for home use and improves the user-adherence compared to known devices of this type. It is furthermore an object to provide a corresponding rehabilitation method.

According to a first aspect of the present invention, a rehabilitation system for a patient suffering from a damaged muscle and/or nerve is presented, wherein the system comprises:

a brain activity sensor for measuring a patient's brain activity related to controlling the damaged muscle and/or nerve;

a muscle sensor for measuring a muscular activity of the damaged muscle and/or a neural activity of the damaged nerve;

a display for displaying a representation of an affected body part of the patient; and a control unit for determining an intended movement of the affected body part in which the damaged muscle and/or nerve is arranged, and for controlling the display to display a representation of the intended movement, wherein the control unit is configured to determine the intended movement based on the patient's brain activity measured by the brain activity sensor and based on the muscular and/or neural activity of the damaged muscle and/or nerve measured by the muscle sensor.

According to a second aspect of the present invention, a method for rehabilitating a patient suffering from a damaged muscle and/or nerve is provided, wherein the method comprises the steps of:

measuring a patient's brain activity related to controlling the damaged muscle and/or nerve;

measuring a muscular activity of the damaged muscle and/or a neural activity of the damaged nerve;

determining an intended movement of an affected body part in which the damaged muscle and/or nerve is arranged, wherein the intended movement is determined based on the patient's brain activity and based on the muscular and/or neural activity of the damaged muscle and/or nerve; and displaying the intended movement of the affected body part to the patient.

Preferred embodiments of the invention are defined in the dependent claims. It shall be understood that the claimed method has similar and/or identical preferred embodiments as the claimed system and as defined in the dependent claims.

The idea of the present invention is to support the patient in recovering his/her damaged muscle and/or nerve by providing the patient with a visual feedback about the movement he/she intends with the affected body part in which the damaged muscle and/or nerve is arranged. This visual feedback helps the patient to understand more about his/her body and the way of moving the affected body part. In addition, by visualizing the intended movement, the patient is facilitated to perceive at an early stage the positive effects of the therapy. In this way patients are able to visualize the progress in the recovery of their neuro-pathways even before their impaired limb is able to actually move, thereby staying motivated to adhere to their therapy program, and enhancing their chance of rehabilitation success. The visual feedback is provided via a display that displays a representation of the intended movement of the affected body part, e.g. in an image sequence.

One of the central features of the presented system is that the intended movement of the affected body part is not only determined by an analysis of the neural activity within the brain, but also based on the muscular activity of the damaged muscle and/or the neural activity of the damaged nerve. The system thereto measures the patient's brain activity related to controlling the damaged muscle and/or nerve by means of a brain activity sensor, while concurrently measuring the muscular activity of the damaged muscle and/or the neural activity of the damaged nerve by means of a muscle sensor. Both the signals of the brain activity sensor and the signals of the muscle sensor are used to determine how, meaning in which way and to what extend, the patient intends to move the affected body part.

The above-mentioned approach (using both signals regarding neural and muscular activity) provides several advantages: The patient of the brain might be healthy, but it may not act in an optimal way. Calculating/estimating the intended movement of the affected body part based on both brain data and muscle data may thus lead to a more accurate determination of the intended movement, and therefore to a more realistic visualization on the display. A more realistic visualization of the intended movement on the display on the other hand improves the feedback to the patient, such that the recovery of the damaged muscle and/or nerve may be improved with this system. The visual feedback on the display also supports the brain of the patient to associate the given visual stimulus with the neural commands of the brain and the muscular responses of the damaged muscle.

The brain is continuously looking for association and tries to find correlations between brain activity and muscular activity. A well-known statement is "firing together is wiring together". This means that if the brain detects that a stimulation from the environment evokes neural activity in two groups of neurons, the two groups of neurons will be connected. The visualization of the intended movement on the display may thus strengthen the correlations within the brain, and may therefore significantly help to improve the rehabilitation success.

Measuring the muscular activity in addition to the brain activity furthermore provides the advantage that the recovery progress of the damaged muscle and/or nerve may be tracked over time, such that the patient may receive a feedback regarding the recovery progress by means of the presented system. This might especially be helpful in an early stage of the rehabilitation therapy. Patients may in this way perceive progress of the therapy even before their impaired limbs including the damaged muscle and/or nerve are able to actually move. Hence, patients may stay motivated to adhere to the therapy program, such that the chance of rehabilitation success is enhanced.

The determination of the intended movement of the affected body part may be based on a calculation/estimation in which the signals of the muscle sensor and the brain activity sensor are added together. This calculation may also include a weighted average of the signals of the muscles sensor and the signals of the brain activity sensor. Since it is especially at the beginning of the recovery process expected that the muscle sensor will deliver no or at least less signals than the brain activity sensor, the muscle sensor may be also configured to measure the muscular activity of muscles arranged in the proximity of the damaged muscle. This allows improving the determination of the intended movement of the affected body part especially at the beginning of the recovery process. If the damaged muscle and/or nerve recover step by step during the therapy, the muscle sensor will deliver more and more accurate signals, such that the accuracy of the determination of the intended movement of the affected body part may even be increased during the ongoing therapy.

The control unit is preferably configured to control the display to display the representation of the intended movement by moving the representation of the affected body part of the patient in real-time on the display. This means that the intended movement is not only visualized by means of an arrow or other graphical symbol on the display, but by moving the representation of the affected body part in a realistic manner on the display, e.g. in a small video sequence. The term "real-time" in this context means that this visualization is provided concurrently to the measurement of the brain activity and the muscular activity. This increases the reality effect for the patient and helps the patient's brain to find associations in the way explained above.

The representation on the display may not only include the affected body part, but also the whole body of the patient. As it will be elucidated further below, the control unit may control the display to display an avatar mirroring the patient. This avatar so to say virtually shows the movement of the affected body part that the patient is intending. The avatar in other words acts as a "movement educator".

It is important to note that the movement of the avatar shown on the display is not necessarily equal to the "real" movement of the patient's body part. As long as the muscle and/or nerves within said body parts are impaired/damaged, the "real" movement of the body part will be less intense than the intended movement shown on the display. This is why brain activity and muscular activity have to be analyzed both for determining the intended movement of the patient.

According to an embodiment, the system further includes a headgear, wherein the brain activity sensor is arranged at or embedded into the headgear. The brain activity sensor may thus be realized as a portable, wearable component. This results in a non-invasive device that disturbs the patient as few as possible.

The headgear preferably comprises one of a belt, strap, band, gear or harness that is configured to be worn on the head of the patient. For example, the headgear may be realized as a stretchable strap that may be worn on the head of the patient.

The brain activity sensor comprises at least one electroencephalographic (EEG) electrode for recording the electrical activity along the scalp of the patient. In practice, the brain activity sensor will comprise a plurality of EEG electrodes placed at different positions of the scalp of the patient, as this is known from many other applications in this technical field. These EEG electrodes measure voltage fluctuations resulting from ionic current flows within the neurons of the brain. The afore-mentioned monitoring of the patient's brain activity is done in the known way by analyzing the spectral content of the EEG signals, i.e. the type of neural oscillations observed in the signals provided by the EEG electrodes.

The muscle sensor preferably comprises at least one electromyographic (EMG) electrode. This EMG sensor is preferably arranged at or embedded into a body attachment component that is configured to worn on a limb of the patient. For example, the body attachment component may be realized as a stretchable strap that may be worn on a leg or an arm of the patient.

According to a further embodiment, the system may comprise a sound generation unit, wherein the control unit is configured to control the sound generation unit to generate a sound indicative of the intended movement.

In this case the patient will not only receive a visual feedback via the display, but also an audible feedback via the sound generation unit. The sound generation unit may, for example, include a loudspeaker that produces a sound which is indicative of the intended movement. The term "intended movement" again refers to the movement of the affected body part that is determined by means of the control unit based on the patient's brain activity measured by the brain activity sensor and based on the muscular and/or neural activity of the damaged muscle and/or nerve measured by the muscle sensor. For example, the control unit may be configured to control the sound generation unit to generate a sound, wherein the type and/or the sound level is adapted to the type and/or intensity of the determined movement of the affected body part. The sound is preferably provided concurrently to the visual simulation on the display as well as concurrently to the brain commands and muscular responses of the patient. Such a multi-sensorial simulation of the patient improves the recovery process of the damaged muscle and/or nerve even more.

In order to further increase the multi-sensorial stimulation effect, the system may furthermore comprise a tactile stimulation unit for stimulating the damaged muscle and/or nerve by means of tactile stimulation.

According to an embodiment, the stimulation unit may comprise at least one of (i) a vibration element for stimulating the damaged muscle and/or nerve by means of vibration and (ii) a thermo element for stimulation the damaged muscle and/or nerve by means of heat and/or cold. The stimulation unit may be arranged at or embedded into the above-mentioned attachment component into which the muscle sensor may be embedded as well.

The additional tactile stimulation unit is preferably controlled by the control unit. The tactile stimulation may either be provided separately (at another instant of time than the visualization of the intended movement on the display, i.e. before or after said visualization), or it may be provided concurrently with the visualization of the intended movement on the display. In the first case, the system may be switchable between two modes, a stimulation mode and a limb exercise mode. In the stimulation mode the damaged muscle and/or nerve is stimulated by means of the stimulation unit. In the limb exercise mode the patient may train the damaged muscle and/or nerve in the above-mentioned way using the display on which the determined intended movement is visualized. In the second case, when the tactile stimulation is provided concurrently with the visualization on the display, the control unit may be configured to control the tactile stimulation unit to adapt the tactile stimulation based on the patient's brain activity measured by the brain activity sensor and/or based on the muscular activity of the damaged muscle measured by the muscle sensor.

According to a further embodiment, the system may further comprise a database for storing a plurality of measurement results of the brain activity sensor and/or the muscle sensor, and an evaluation unit for comparing the plurality of measurement results with each other in order to determine a recovery progress of the patient.

This allows measuring the patient's brain activity and/or the patient's muscular activity at different instants of time during the therapy, such that the system (the evaluation unit) may calculate statistics regarding the recovery progress in the limb muscle responses. The evaluation unit may, for example, be configured to compare the difference of the signals of brain activity and the muscular activity measured at one instant of time $t_1$ to the difference of the signals of the brain activity and the muscular activity measured at a second instant of time $t_2$ ($t_1+\Delta t$).

In this embodiment, the control unit may be furthermore configured to control the display to display a visual indicator that is indicative of the recovery progress of the patient. The patient may thus receive a visual feedback on the display regarding the recovery progress. This may help to motivate the patient especially in the beginning of the therapy when the patient does not perceive any progress him/herself, while the progress is already measurable by the brain activity sensor and the muscle sensor. The user-adherence may thus be further improved, since the patient receives a positive feedback and may at least visually perceive the effect of the therapy.

In a further embodiment, the rehabilitation system may further comprise a reward unit to display a visual reward and/or for controlling the sound generation unit to produce an audible reward based on the recovery progress determined by the evaluation unit. The patient may thus get a positive feedback by means of a graphical symbol displayed on the display and/or by means of encouragement comments, music or sounds generated by the sound generation unit that motivate him/her to keep on training the damaged muscle and/or nerve.

According to a further embodiment, the system may comprise a therapy unit for determining a suggested stimulation for stimulating the damaged muscle and/or nerve, wherein said suggested stimulation is based on the plurality of measurement results of the brain activity sensor and/or the muscle sensor stored in the database. The therapy unit may be configured to control the display to display a visual indicator explaining (either graphically or in text form) the suggested stimulation to the patient. This may include suggestions regarding which limbs should be given priority to be exercised more in the coming days, weeks or months. The therapy may thus be adapted to the personal needs of the patient.

The therapy unit may also be connected to the tactile stimulation unit in order to control the tactile stimulation unit based on the plurality of measurement results of the brain activity sensor and/or the muscle sensor. In other words, the therapy unit may be configured to control the stimulation unit for stimulating the damaged muscle and/or nerve by means of tactile stimulation, wherein the tactile stimulation is based on the plurality of measurement results of the brain activity sensor and/or the muscle sensor stored in the database. The therapy is thus automatically adapted to the patient's needs.

According to a further embodiment, the rehabilitation system may furthermore comprise a database for storing a plurality of measurement results of the brain activity sensor and/or the muscle sensor, and an evaluation unit for comparing the plurality of measurement results with corresponding reference measurement results of at least one other patient.

The database may, for example, include a remotely arranged database that is accessible by the rehabilitation system via the internet. If other users use the same or a similar type of rehabilitation system, the therapy progress of the patient at hand may be compared to the other patients. The evaluation unit may in this case be configured to control the display to display a visual indicator that is indicative of the comparison of the measurement results of the patient with the measurement results of the other patients. Hence, the patient may receive a feedback how he/she performs compared to other patients having the same or similar disease. For example, statistical comparisons between the patient at hand and other patients may be displayed on the display.

In a further embodiment, the control unit is configured to control the display to display an avatar, wherein the avatar includes the representation of the affected body part. Such an avatar appears to be more realistic for the patient than just simply showing a video sequence of the movement of a visual representation affected body part on the display.

In a refinement, the rehabilitation system may further comprise an input interface for receiving anatomical information of the patient, wherein the control unit is configured to control the display to adapt the avatar based on the anatomical information of the patient.

In this case, the visualized avatar so to say mirrors the "real" patient's appearance and shows the intended movement of the affected body part of the patient in a realistic way. The avatar may, for example be visualized in real-size on the display. The above-mentioned input interface allows to input a picture of the patient or his/her face as well as to input the height, weight and/or other anatomical characteristics of the patient, such that the control unit may generate an avatar that resembles the appearance of the patient best.

BRIEF DESCRIPTION OF THE DRAWINGS

These and other aspects of the invention will be apparent from and elucidated with reference to the embodiments described hereinafter. In the following drawings

DETAILED DESCRIPTION OF THE INVENTION

Figure 1A:
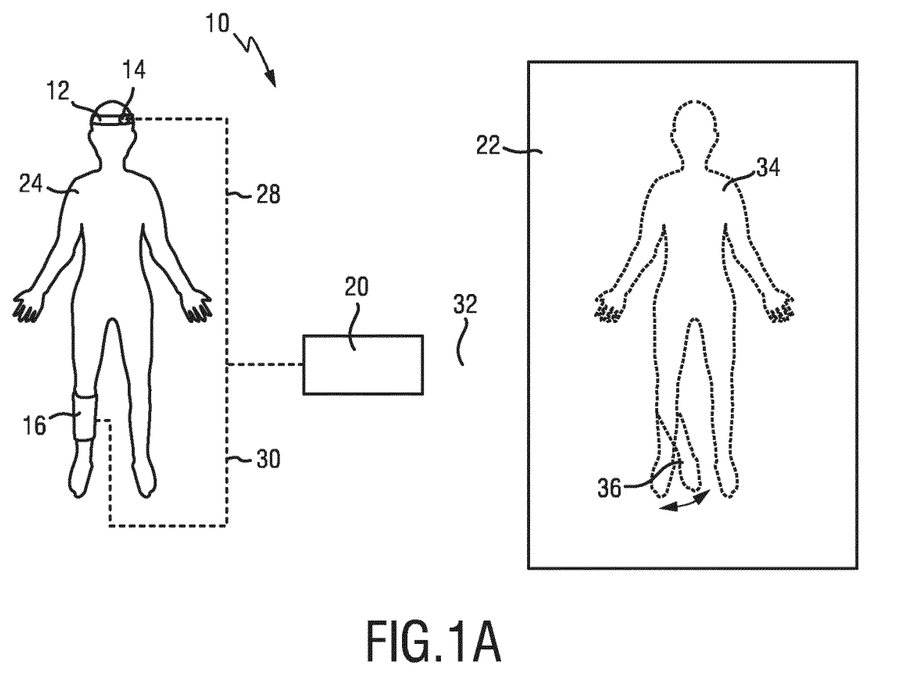
FIG. 1A shows a schematic view of a first embodiment of a rehabilitation system according to the present invention.

FIG. 1A shows a first embodiment of a rehabilitation system according to the present invention. The rehabilitation system is therein denoted in its entirety with reference numeral 10.

Figure 1B:
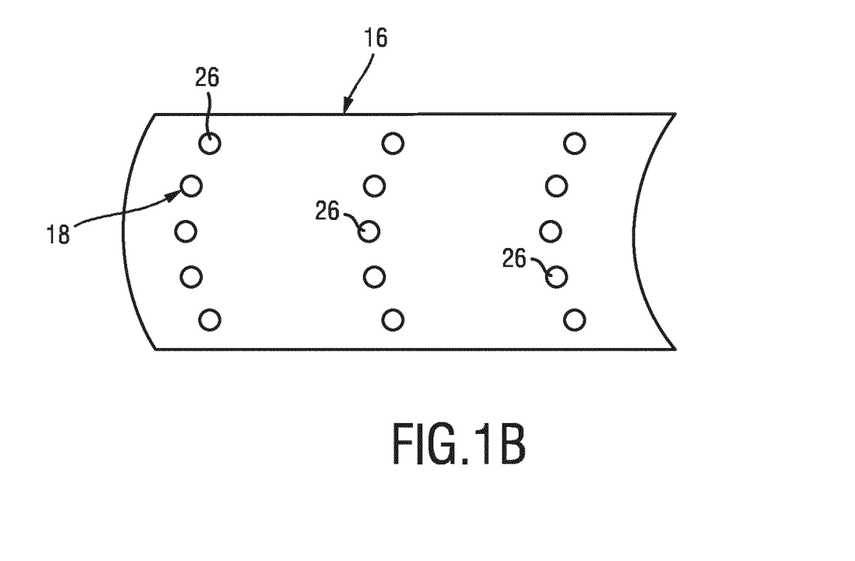
FIG. 1B shows a schematic view of a body attachment component including a muscle sensor of the rehabilitation system according to the first embodiment.

The rehabilitation system 10 comprises a headgear 12 including a brain activity sensor 14, a body attachment component 16 including a muscle sensor 18, a control unit 20 and a display 22. An enlarged schematic view of an exemplary body attachment component 16 including the muscle sensor 18 is shown in FIG. 1B.

The headgear 12 is configured to be worn on the head/scalp of a patient 24. The headgear 12 is preferably realized as a strap, band or cap at which the brain activity sensor is arranged or into which the brain activity sensor 14 is embedded. The brain activity sensor preferably comprises a plurality of encephalographic (EEG) electrodes that are configured to measure the brain activity of the patient 24. Such EEG electrodes are well-known in the art and shall thus not be further detailed in the following.

The body attachment component 16 is realized as a wearable component that may be worn on one of the limbs of the patient 24, i.e. on an arm or a leg of the patient 24. According to a preferred embodiment, said body attachment component preferably comprises one of a belt, strap, band, gear or harness that is made of an elastic material, such that the body attachment component 16 fits to an arm as well as to a leg of the patient 24, wherein the patient 24 does not have to manually adapt its size. The muscle sensor 18 preferably comprises a plurality of electromyographic (EMG) electrodes 26 which are arranged at or embedded into the body attachment component 16. These EMG electrodes 26 are configured to measure a muscular and/or neural activity of a damaged muscle and/or nerve of the patient 24.

The control unit 20 may be realized as a processor, microprocessor or computer having software stored thereon for controlling the display 22 according to the principle of the present invention, as this will be elucidated in detail further below.

The display 22 may comprise a screen, such as a monitor with a cathode ray tube, a LCD monitor, a plasma monitor or any other type of monitor. Alternatively, the display 22 may comprise a projector or beamer for projecting images onto a wall or screen.

The control unit 20 is connected to the brain activity sensor 14, to the muscle sensor 18 as well as to the display 22. The connection 28 between the control 20 and the brain activity sensor 14 as well as the connection 30 between the control unit 20 and the muscle sensor 18 as well as the connection 32 between the control unit 20 and the display 22 may either be hard-wired or wireless (e.g. using a Bluetooth®, an infrared, a WLAN or near field communication technique). Even though the control unit 20 is in FIG. 1A shown as a separate unit that is arranged remotely from the headgear 12, the body attachment component 16 and the display 22, parts of the control unit 20 or the whole control unit 20 may be integrated into or arranged at the headgear 12, the body attachment component 16 or the display 22.

The presented system 10 addresses patients 24 with a generally healthy neuro-activity necessary for limbic motion, but damaged muscles and/or muscle nerves. The system 10 should help such patients 22 to revitalize the muscle tonus and/or muscle nerves necessary for limbic motion. The system shall particularly help such patients 24 to exercise their limbs in which the damaged muscles and/or muscle nerves are arranged.

The patient 24 receives a visual feedback on the display 22 that shows him/her how to move the limb comprising the damaged muscles and/or nerves. The control unit 20 receives the measurement signals from the brain activity sensor 14 and the muscle sensor 18. From these signals the control unit 20 determines an intended movement of the body part in which the damaged muscles and/or nerves are arranged.

In other words, the control unit 20 is configured to determine the intended movement of the affected body part based on both the patient's brain activity and the muscular and/or neural activity of the damaged muscles and/or nerves. The term "intended movement" thereby denotes the movement of the affected body part that is estimated/calculated based on both of these signals.

A central feature of the system 10 is the visualization of this intended movement on the display 22. The display 22 thereto displays a representation 34 of the affected body part of the patient 24. In a preferred embodiment, the display 22 is configured to display an avatar that mirrors the anatomical appearance of the patient 24. However, in some cases it might also be sufficient to display only a graphical representation of the affected body part of the patient 24 on the display 22.

The control unit 20 furthermore controls the display 22 to display a graphical representation 36 of the intended movement by moving the representation 34 of the affected body part of the patient 24 in real-time on the display 22. The intended movement, which is calculated based on both the signals of the brain activity sensor 14 and the muscle sensor 18, may e.g. be visualized to the user by means of a small video sequence. Said video sequence may show the calculated movement of the affected limb (in the example shown in FIG. 1A the movement of the right leg) on the display 22. The control unit 20 thus controls the visualized avatar 34 to execute the intended limb movement that is determined from the on-going neuro-activity involved in the movement process.

Again it shall be noted that the intended movement is determined from both the neuro-activity in the motor cortex associated with said intended movement as well as from the muscular activity measured by means of the muscle sensor 18. Taking both of these signals allows a more accurate determination of the intended movement. Including the signals of the muscle sensor 18 into this determination as well furthermore allows tracking the recovery process of the damaged muscles and/or nerves over time. The EEG electrodes of the brain activity sensor 14 send the patient's neuro-activity initiated as a part of the command from the brain to the limb, whereas the EMG electrodes 26 of the muscle sensor 18 sends the level of response in the limb muscles.

The graphical visualization of the intended movement on the display 22 does not only teach the patient 24 how to move the affected limb, but may also give him/her a visual feedback on his neural and muscular activity regarding the affected body part. The control unit 20 is preferably configured to determine the intended movement by adding the signals of the brain activity sensor 14 and the muscle sensor 18. This determination may also include a weighted average of both of these signals. At the beginning of the recovery process the muscle sensor 18 will most probably add only minor signal parts, since the level of response of the limb muscles that is sensed via the EMG electrodes 26 is in this stage normally rather low (due to the muscle being still impaired). However, during the therapy it is expected that the level of response sensed by the EMG electrodes 26 increases more and more, such that the signals of the muscle sensor 18 increasingly participate to the determination of the intended movement over time. In order to increase the accuracy of the movement determination, the muscle sensor 18 may be configured to also measure the muscular activity of neighboring muscles that are not damaged. The control unit 20 may thus at the beginning also use the signals of the neighboring muscles in addition to the signals of the brain activity sensor 14 for determining the intended movement that is concurrently displayed on the display 22.

Figure 2A:
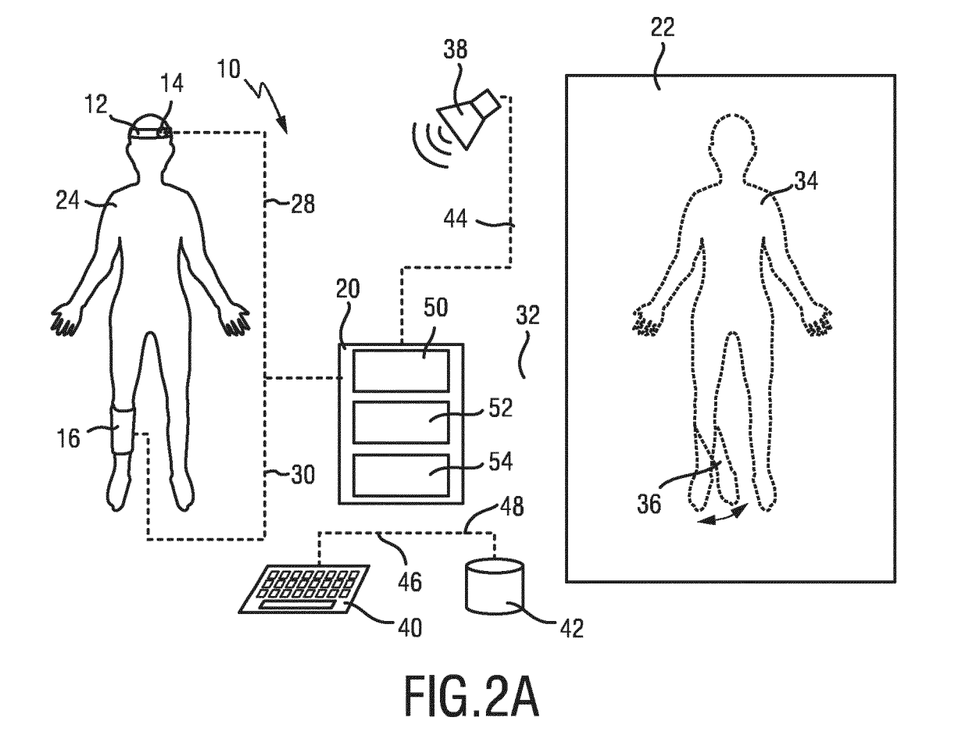
FIG. 2A shows a schematic view of a second embodiment of the rehabilitation system according to the present invention.
Figure 2B:
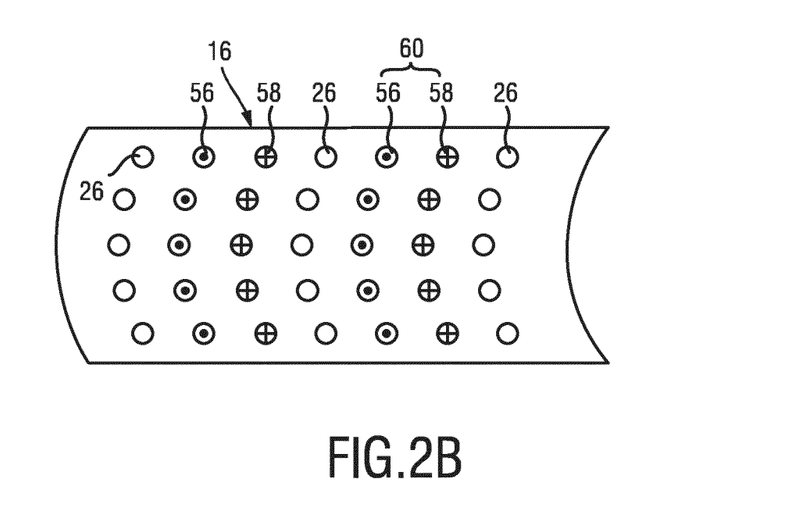
FIG. 2B shows a schematic view of the body attachment component including the muscle sensor of the rehabilitation system according to the second embodiment.

FIGS. 2A and 2B show a second embodiment of the system 10 according to the present invention. Same or similar components are therein denoted by the same reference numerals as before. These already presented components shall not be explained again.

Additionally to the components of the system 10 according to the first embodiment, the system 10 according to the second embodiment further comprises a sound generation unit 38, an input interface 40 and a database 42. The sound generation unit 38, the input interface 40 and the database 42 are connected to the control unit 20. The connections 44, 46, 48 between these components 38, 40, 42 and the control unit 20 may again be realized either as hard-wired connections or as wireless connections.

The sound generation unit 38 may, for example, comprise a loudspeaker or any other type of device for generating sounds. The input interface 40 may comprise a keyboard, mouse, an USB-interface or any other type of data interface that allows a user to input or transfer data to the control unit 20. The input interface 40 may also be used to adapt the settings of the control unit 20. The database 42 may include any type of storage means, such as a hard drive that is accessible by the control unit 20 by any type of data network, e.g. a local area network (LAN) or the internet. The database 42 may also be part of a computer that includes the control unit 20.

The control unit 20 may according to the second embodiment shown in FIG. 2A furthermore comprise several sub-units: an evaluation unit 50, a reward unit 52 and a therapy unit 54. All of these units 50, 52, 54 may be part of the control unit 20. However, the evaluation unit 50, the reward unit 52 and the therapy unit 54 may alternatively also be realized as separate entities. In practice, these units 50, 52, 54 are preferably realized as integrated parts of the control unit 20 and are software- and/or hardware-based.

The addition of the sound generation unit 38 enables to produce sounds congruently with the visual stimulation (representation 36 of the intended movement) on the display 22. The control unit 20 may control the sound generation unit 38 to generate a sound that is indicative of the intended movement. The type and/or loudness of this sound may be adapted to the type and/or intensity of the determined intended movement. The sound generated by the sound generation unit 18 is also based on the signals of the brain activity sensor 14 and the muscle sensor 16. The sensorial stimulation of the patient 24 is thus expanded to one additional stimulus (an audible stimulus).

The input interface 40 may, for example, be used to input a picture of the patient 24, a height of the patient 24, a weight of the patient 24 and/or an indication of the built of the patient 24 (lean/medium/heavy). The graphical representation 34 of the avatar may thus be based on the anatomical information of the patient 24 that are received via the input interface 40. This provides an even more realistic feeling for the patient, since the avatar in this case mirrors the patient 24 in a graphical form as realistic as possible.

The database 42 may be used for storing the measurement results of the brain activity sensor 14 and/or the muscle sensor 18. Storing these measurement results allows evaluating the recovery process of the patient 24 over time. The evaluation unit 50 is configured to compare the measurement results gathered over time with each other in order to determine a recovery progress of the patient 24. The evaluation unit 50 may, for example, calculate statistics regarding the recovery process in the limb muscles by comparing the level of response measured by the EMG electrodes at the beginning of the therapy with the level of response measured by the EMG electrodes 26 at a later stage of the therapy. This statistic may help the patient 24 to perceive the benefits of the therapy. The display 22 may display a dashboard indicating the activity level of the damaged muscle and/or nerve together with trends over time. The evaluation unit 50 may also be configured to compare the difference of the brain activity signals and the muscle signals over time in order to generate a statistic including the trend of this difference over time. If said difference decreases over time, this may be an indicator of a positive effect of the therapy.

The reward unit 52 may be configured to control the display 22 to display a visual indicator that is indicative of the recovery process evaluated by the evaluation unit 50. This may help to motivate the patient 24 to proceed with the therapy. If the evaluation unit 50 determines a positive recovery progress of the patient 24, the reward unit 52 could display a graphical item for motivating the patient 24. The reward unit 52 may also be configured to control the sound generation unit 38 to produce a corresponding sound that gives the patient 24 a feedback regarding the recovery process. The sound generation unit 38 may, for example, output encouragement comments which celebrate the success by means of an audible sensory reward.

The database 42 may be also used to store a plurality of reference measurement results of brain activity sensors and/or muscle sensors of the type mentioned above which belong to other patients. This may help to compare the measurement results of the patient 24 at hand with the reference measurement results of the other patients. The evaluation unit 50 may thereto be configured to compare the measurement results of the patient 24 with corresponding reference measurement results of the other patients and to control the display 22 to display a visual indicator that is indicative of said comparison. This visual indicator may comprise a statistical comparison including a table or dashboard.

As shown in FIG. 2A, the control unit 20 may according to the second embodiment also comprise a therapy unit 54. This therapy unit 54 may be configured to determine a suggested stimulation for stimulating the damaged muscle and/or nerve, wherein said suggested simulation is based on the plurality of measurement results of the brain activity sensor 14 and/or the muscle sensor 18. The therapy unit 54 may be configured to control the display 22 and/or the sound generation unit 38 to output suggestions how to train the affected body part of the patient 24 best.

As shown in FIG. 2B, the body attachment component 16 comprises according to the second embodiment not only the EMG electrodes 26 of the muscle sensor 18, but also a tactile stimulation unit 60 including plurality of vibration elements 56 and a plurality of thermo elements 58. The vibration elements 56 may stimulate the damaged muscle and/or nerve of the patient 24 by means of vibration. The thermo elements 58 may stimulate the damaged muscle and/or nerve of the patient 24 by means of heat and/or cold. These vibration elements 56 and thermo elements 58 may be controlled by means of the control unit 20. According to a first alternative, the system 10 may be switchable between two different modes, a simulation mode, in which the damaged muscle and/or nerve is stimulated by means of the vibration element 56 and/or the thermo elements 58, and a limb exercise mode, in which the patient 24 is shown the intended movement on the display as explained before. According to a second alternative, the vibration elements 56 and/or the thermo elements 58 may be controlled by means of the therapy unit 54. In other words, the vibration elements 56 and/or the thermo elements 58 are in this case automatically controlled based on the measurement results of the brain activity sensor 14 and/or the muscle sensor 18, such that a closed-loop system is realized.

Figure 3:
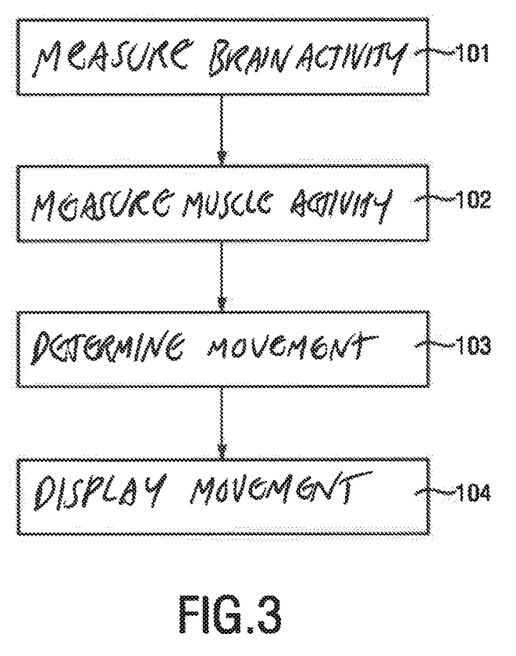
FIG. 3 shows a schematic diagram illustrating a method for rehabilitating a patient according to the present invention.

FIG. 3 summarizes the method according to the present invention in a schematic manner. In a first step 101, a patient's brain activity related to controlling the damaged muscle and/or nerve is measured by means of a brain activity sensor 14. In a second step 102, a muscular and/or neural activity of the damaged muscle and/or nerve is measured by means of a muscle sensor 16. In a third step 103, an intended movement of an affected body part in which the damaged muscle and/or nerve is arranged is determined. The intended movement is determined based on the patient's brain activity and based on the muscular and/or neural activity of the damaged muscle and/or nerve. In the fourth and last step 104, the intended movement of the affected body part is shown to the patient on a display 22.

It shall be noted that the additional and alternative embodiments mentioned above with reference to FIGS. 1 and 2 may be included in the presented method as well.

It shall be noted that FIG. 3 shows the presented method for simplicity reasons in a sequential form. However, steps 101-104 are in practice carried out concurrently.

Lastly, it shall be also noted that the components of the second embodiment of the system 10, which were not elucidated with reference to the first embodiment shown in FIG. 1, do not necessarily have to be provided altogether. For example, the sound generation unit 38, the input interface 40 and the database 42 are independent parts. The system 10 may therefore also comprise only one of these components. The body attachment component 16 may similarly comprise only one of the vibration elements 56 and the thermo elements 58.

While the invention has been illustrated and described in detail in the drawings and foregoing description, such illustration and description are to be considered illustrative or exemplary and not restrictive; the invention is not limited to the disclosed embodiments. Other variations to the disclosed embodiments can be understood and effected by those skilled in the art in practicing the claimed invention, from a study of the drawings, the disclosure, and the appended claims.

In the claims, the word "comprising" does not exclude other elements or steps, and the indefinite article "a" or "an" does not exclude a plurality. A single element or other unit may fulfill the functions of several items recited in the claims. The mere fact that certain measures are recited in mutually different dependent claims does not indicate that a combination of these measures cannot be used to advantage.

Any reference signs in the claims should not be construed as limiting the scope.

The invention claimed is:

1. A rehabilitation system for a patient suffering from a damaged muscle, said rehabilitation system comprising:
   a brain activity sensor configured to measure a patient's brain activity related to controlling the damaged muscle;
   a muscle sensor configured to measure a muscular activity of the damaged muscle;
   a display configured to display a representation of an affected body part of the patient;
   a control unit configured to
      determine an intended movement of the affected body part with the damaged muscle,
      control the display to display a representation of the intended movement, and
      determine the intended movement based on both the patient's brain activity measured by the brain activity sensor and the muscular activity of the damaged muscle measured by the muscle sensor; and
   an evaluation unit configured to
      compare a plurality of measurement results of the patient's brain activity measured by the brain activity sensor and the muscular activity of the damaged muscle measured by the muscle sensor over time to determine a recovery progress of the patient and a difference between the brain activity signals and the muscle signals over time;
      generate a statistic including a trend of brain activity signals and muscle signals over time, wherein a decrease in the difference between the brain activity signals and the muscle signals over time indicates a positive effect of a therapy; and
      display the statistic to the patient with a graphical item to provide feedback to the patient regarding recovery.

2. The rehabilitation system according to claim 1, wherein the control unit is further configured to control the display to display the representation of the intended movement by moving the representation of the affected body part of the patient in real-time on the display.

3. The rehabilitation system according to claim 1, wherein the brain activity sensor further comprises:
   at least one electroencephalographic (EEG) electrode.

4. The rehabilitation system according to claim 1, further comprising:
   a headgear, wherein the brain activity sensor is arranged at or embedded into the headgear.

5. The rehabilitation system according to claim 1, wherein the muscle sensor further comprises:
   at least one electromyographic (EMG) electrode.

6. The rehabilitation system according to claim 1, further comprising:
   a sound generation unit, wherein the control unit is further configured to control the sound generation unit to generate a sound indicative of the intended movement.

7. The rehabilitation system according to claim 1, further comprising:
   a tactile stimulation unit configured to stimulate the damaged muscle by means of tactile stimulation.

8. The rehabilitation system according to claim 7, wherein the tactile stimulation unit comprises at least one of
   (i) a vibration element configured to stimulate the damaged muscle by means of vibration and
   (ii) a thermo element configured to stimulate the damaged muscle by means of heat and/or cold.

9. The rehabilitation system according to claim 1, further comprising:
   a database configured to store the plurality of measurement results of both the brain activity sensor and the muscle sensor.

10. The rehabilitation system according to claim 9, wherein the control unit is further configured to control the display to display a visual indicator that is indicative of the recovery progress of the patient.

11. The rehabilitation system according to claim 9, further comprising:
    a therapy unit configured to determine a suggested stimulation for stimulating the damaged muscle, said suggested stimulation being based on the plurality of measurement results of both the brain activity sensor and the muscle sensor.

12. The rehabilitation system according to claim 1, further comprising:
    a database configured to store a plurality of measurement results of both the brain activity sensor and the muscle sensor, wherein the evaluation unit is further configured to compare the plurality of measurement results with corresponding reference measurement results of at least one other patient.

13. The rehabilitation system according to claim 1, wherein the control unit is further configured to control the display to display an avatar, wherein the avatar includes the representation of the affected body part.

14. The rehabilitation system according to claim 13, further comprising:
    an input interface configured to receive anatomical information of the patient, wherein the control unit is further configured to control the display to adapt the avatar based on the anatomical information of the patient.

15. The rehabilitation system of claim 1, wherein the control unit is further configured to add signals of the brain activity sensor to signals of the muscle sensor.

16. The rehabilitation system of claim 1, wherein the control unit is further configured to determine a weighted average of signals of the brain activity sensor and signals of the muscle sensor.

17. The rehabilitation system of claim 1, wherein the muscle sensor is further configured to measure muscular activity of neighboring muscles that are not damaged.

18. A method for rehabilitating a patient suffering from a damaged muscle, said method comprising:
    measuring a patient's brain activity related to controlling the damaged muscle;
    measuring a muscular activity of the damaged muscle;
    comparing a plurality of measurement results of both the patient's brain activity and muscular activity over time to determine a recovery progress of the patient and a difference between the brain activity signals and the muscle signals over time;
    generating a statistic including a trend of the patient's brain activity and the muscular activity over time, wherein a decrease in the difference between the patient's brain activity and the muscular activity over time indicates a positive effect of a therapy;
    displaying the statistic to the patient with a graphical item to provide feedback to the patient regarding recovery;
    determining an intended movement of an affected body part with the damaged muscle, wherein the intended movement is determined based on both the patient's brain activity and the muscular activity of the damaged muscle; and displaying the intended movement of the affected body part to the patient.

* * * * *